United States Patent
Sutton et al.

[19]

[11] Patent Number: 6,129,683
[45] Date of Patent: Oct. 10, 2000

[54] OPTICAL BIOPSY FORCEPS

[75] Inventors: Gregg S. Sutton, Plymouth; Brian T. McMahon, Minnetonka, both of Minn.

[73] Assignee: SpectraScience, Inc., Plymouth, Minn.

[21] Appl. No.: 08/975,734

[22] Filed: Nov. 21, 1997

Related U.S. Application Data

[63] Continuation of application No. 08/644,080, May 7, 1996, Pat. No. 5,762,613.

[51] Int. Cl.⁷ .................................................. A61B 10/00
[52] U.S. Cl. ......................... 600/564; 606/207; 606/208
[58] Field of Search .................................. 600/564, 565, 600/566

[56] References Cited

U.S. PATENT DOCUMENTS

| | | | |
|---|---|---|---|
| 3,074,408 | 1/1963 | Chester | 128/328 |
| 3,924,608 | 12/1975 | Mitsui | 128/2 B |
| 3,961,621 | 6/1976 | Northeved | 128/2 B |
| 4,027,510 | 6/1977 | Hiltebrandt | 72/37 |
| 4,421,106 | 12/1983 | Uehara | 128/4 |
| 4,557,255 | 12/1985 | Goodman | 128/7 |
| 4,573,450 | 3/1986 | Arakawa | 128/6 |
| 4,620,547 | 11/1986 | Boebel | 128/754 |
| 4,646,751 | 3/1987 | Maslanka | 128/751 |
| 4,656,999 | 4/1987 | Storz | 128/4 |
| 4,887,612 | 12/1989 | Esser et al. | 128/751 |
| 5,228,451 | 7/1993 | Bales et al. | 128/751 |
| 5,280,788 | 1/1994 | Janes et al. | 128/665 |
| 5,291,010 | 3/1994 | Tsuji | 250/208.1 |
| 5,318,023 | 6/1994 | Vari et al. | 128/633 |
| 5,354,291 | 10/1994 | Bales et al. | 604/35 |
| 5,373,854 | 12/1994 | Kolozsi | 128/749 |
| 5,439,000 | 8/1995 | Gunderson et al. | 128/664 |
| 5,471,992 | 12/1995 | Banik et al. | 128/751 |
| 5,482,054 | 1/1996 | Slater et al. | 128/751 |
| 5,536,248 | 7/1996 | Weaver et al. | 604/54 |
| 5,558,100 | 9/1996 | Cox | 128/751 |
| 5,562,102 | 10/1996 | Taylor | 128/751 |
| 5,571,129 | 11/1996 | Porter | 606/170 |
| 5,667,473 | 9/1997 | Finn et al. | 600/104 |
| 5,762,613 | 6/1998 | Sutton et al. | 600/564 |
| 5,843,000 | 12/1998 | Nishioka et al. | 600/566 |
| 5,848,978 | 12/1998 | Cecchi | 600/567 |
| 5,857,961 | 1/1999 | Vanden Hoek et al. | 600/104 |
| 5,908,381 | 6/1999 | Aznoian et al. | 600/104 |

FOREIGN PATENT DOCUMENTS

| | | |
|---|---|---|
| 316816 | 11/1988 | European Pat. Off. ............... 600/182 |
| 0321132 | 6/1989 | European Pat. Off. . |
| 0 593 929 | 4/1994 | European Pat. Off. ........ A61B 17/00 |
| 3920706A1 | 1/1991 | Germany ........................ A61B 17/28 |
| 195 33 856 | 3/1997 | Germany ........................ A61B 19/00 |
| WO83/03189 | 9/1983 | WIPO . |
| WO94/12095 | 6/1994 | WIPO . |
| 91/41776 | 11/1997 | WIPO ............................ A61B 10/00 |

OTHER PUBLICATIONS

"Copy of International Search Report", by R. Gimenez Burgos for Application No. PCT/US 97/07624, 2 pages, (Jul. 22, 1997).

"Copy of International Search Report", by J. Weihs for Application No. PCT/US 97/07784, 2, (Aug. 22, 1997).

*Primary Examiner*—Cary E. O'Connor
*Assistant Examiner*—Pamela Wingood
*Attorney, Agent, or Firm*—Schwegman, Lundberg, Woessner & Kluth, P.A.

[57] ABSTRACT

An integrated optical biopsy forceps device and a method for tissue identification by optical analysis and biopsy sampling at a site within the body. The device includes an elongated catheter body for introduction into the body and navigation to an area of interest. An optical fiber extends through the device, from the proximal end, where it may be connected to electro-optical spectral analysis equipment, to a distal tip for illuminating and receiving light energy from tissue at the location of the tip. The distal end of the device has a pair of cutting jaws pivotally mounted at the distal end of the catheter body and controlled by control wires extending through the catheter body to a control handle at the proximal end, or by the optical fiber. The device may be spectroscopically guided to a site of interest within the body. The fiber tip is positioned coaxially with the jaws at the zone of contact and cutting of the jaws, and is retracted as the jaws close, so that the biopsy sample is taken exactly at the spot being viewed by the optical fiber.

6 Claims, 7 Drawing Sheets

OPTICAL BIOPSY FORCEPS

This application is a continuation of U.S. patent application Ser. No. 08/644,080, filed May 7, 1996, now U.S. Pat. No. 5,762,613.

FIELD OF THE INVENTION

This invention pertains to the field of medical diagnosis and treatment. More specifically, the invention pertains to a forceps device having integrated optical fiber and remotely controllable biopsy forceps functions, and to the use thereof in medical diagnosis. The catheter is adapted for in vivo tissue identification of tissue types through optical techniques using the optical fiber, and biopsy sampling of identified tissue areas for withdrawal from the body for conventional examination and analysis.

BACKGROUND OF THE PRIOR ART

Numerous type of biopsy forceps devices have been developed for in vivo medical diagnosis and treatment of various conditions. Such devices are designed for sampling tissue within the body, for example in endoscopic, laparoscopic and vascular procedures to retrieve biopsy samples for analysis and identification of tissue types. These biopsy forceps devices generally include small cutting jaws at the distal end, operated remotely from the proximal end after the distal end of the device has been positioned or navigated to the site of interest.

One difficulty in using prior art biopsy forceps devices is in knowing for certain the exact positioning of the distal tip, in relation to the suspected disease area, especially when the area of interest is very small. Various types of optical catheters or probes have been developed for use in locating or identifying sites within the body. A method of diagnosing and treating tissue in vivo using an optical guidewire is disclosed in U.S. Pat. No. 5,439,000, assigned to SpectraScience, Inc. One type of prior art system for internal biopsy uses an optical catheter to locate the site, followed by replacement of the optical catheter with a biopsy forceps for taking a sample. However, this can result in errors and uncertainties in the final placement of the biopsy jaws with respect to a previously identified small structure or area.

Other prior art systems have been proposed which use optical viewing or imaging and a cutting device in the same device, to visually locate and then biopsy a suspected area. However, such devices have been hampered by their thickness which is needed to accommodate the imaging system and the cutting actuation system, and which precludes their use in very small areas. Another shortcoming of such prior art systems is the offset or 'parallax' between the viewing axis or the imaging system and the cutting position of the biopsy jaws, such that the biopsy sample actually is taken from a zone slightly displaced from the zone being viewed by the optics. This can result in a loss of accuracy in the case of very small structures of interest.

SUMMARY OF THE INVENTION

To overcome these and other problems, the present invention provides an integrated fiber optic biopsy forceps device, which is very thin, enabling it to be used in very small areas of interest, and which has accurate alignment of the optic field of view and the biopsy zone of sampling.

The present invention provides an optical biopsy forceps which is adapted for tissue identification both by optical techniques and biopsy sampling. The forceps device includes an elongated catheter body for introduction into the body and navigation to an area of interest. The distal end of the forceps device has a pair of cutting jaws, and the tip of an optical fiber which runs through the forceps device. The proximal end has a control handle for manipulating the forceps device and actuating the jaws.

In accordance with one aspect of the invention, there is provided a method of diagnosing tissue at a site within a body. The method comprises introducing into the body an integrated optical biopsy forceps which includes a flexible catheter body with an optical fiber extending therethrough with the distal end of the optical fiber positioned with its optical view axis aligned for a tissue analysis zone adjacent the distal tip of the catheter body. The optical biopsy forceps additionally including cutting jaws mounted at the distal end of the catheter body for selective opening and closing in a biopsy cutting movement in the tissue analysis zone, and an actuator mechanism operatively connected to the jaws for selectively controlling the opening and closing of the cutting jaws. Then, tissue in the tissue analysis zone adjacent the distal end of the forceps is spectroscopically analyzed through the use of an electro-optic tissue analysis system connected to the proximal end of the optical fiber. The optical biopsy forceps is spectroscopically guided within the body to an area of interest as identified by the spectroscopic analysis of tissue type in the tissue analysis zone adjacent the distal tip of the catheter body. Then, a biopsy sample is cut from the location of the optical tissue analysis zone by actuating the actuator mechanism, and the biopsy sample is withdrawn from the body.

In one embodiment, the cutting jaws are mounted for pivoting or other movement bringing them together for cutting tissue placed therebetween, and coupled to and controlled by the optical fiber that extends through the catheter body to the handle at the proximal end of the device. The optical fiber extends through the handle and the catheter body from its proximal end for connection to electro-optical analysis equipment, to a distal tip for transmitting and/or receiving light energy from tissue at the location of the tip. The fiber tip is positioned coaxially with the jaws at their zone of contact and cutting, so that the biopsy sample is taken exactly at the spot in the field of view of the optical fiber.

In another embodiment, the cutting jaws are mounted for pivoting or other movement bringing them together for cutting tissue placed therebetween, and controlled by wires extending through the catheter body to the control handle. The optical fiber extends through the device, from its proximal end for connection to electro-optical analysis equipment, to a distal tip for transmitting and/or receiving light energy from tissue at the location of the tip. The fiber tip is positioned coaxially with the jaws at their zone of contact and cutting, so that the biopsy sample is taken exactly at the spot in the field of view of the optical fiber.

One example of the utility of the invention is in the diagnosis of arterial or vascular obstructions, such as atherosclerotic lesions and thrombi. After identification, the appropriate therapeutic catheter, whether balloon angioplasty, drug delivery or laser ablation, can be advanced along a guidewire and employed to treat the patient. The present invention is also useful in many other fields including, but not limited to: oncology, urology, gastroenterology, neurosurgery, general surgery, obstetrics/gynecology, etc. It can also be used in laparoscopic procedures for additional diagnostic information, and/or guidance of a therapeutic modality (e.g., laser or cutting/coagulation devices, such as a bipolar electrocautery device).

Certain aspects of the optical biopsy forceps and method for diagnosing tissue described herein are not the invention of the present inventors, and are included only for completeness. These aspects are claimed in copending application Ser. No. 08/643,912, naming as the inventors Norman S. Nishioka and Kevin T. Schomacker, entitled Optical Biopsy Forceps and Method of Diagnosing Tissue.

These and other features and advantages of the invention will become apparent from the following description of the preferred embodiments of the invention.

DESCRIPTION OF THE PREFERRED EMBODIMENTS

Figure 1:
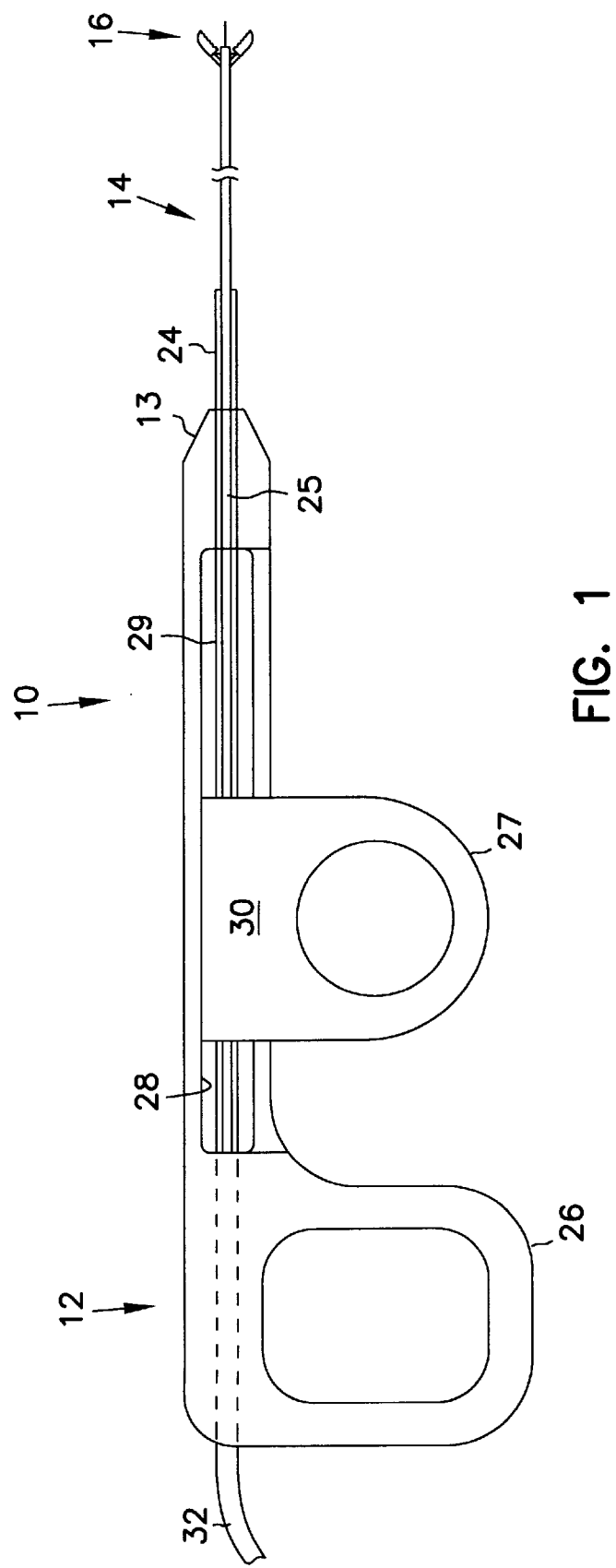
FIG. 1 is an overall view of the optical biopsy forceps according to the present invention.

One preferred embodiment of an integrated optical biopsy forceps of the present invention is generally indicated by reference number 10 in FIG. 1. Forceps 10 is adapted for use internally of the body, for example in connection with endoscopic, laparoscopic or vascular procedures. Forceps 10 includes a control handle portion 12 at the proximal end, a middle portion 14 which extends over the main length of the device, and a distal end 16 which includes opposed forceps cutting jaws and distal end of the optical fiber, as is explained in greater detail below.

Figure 2:
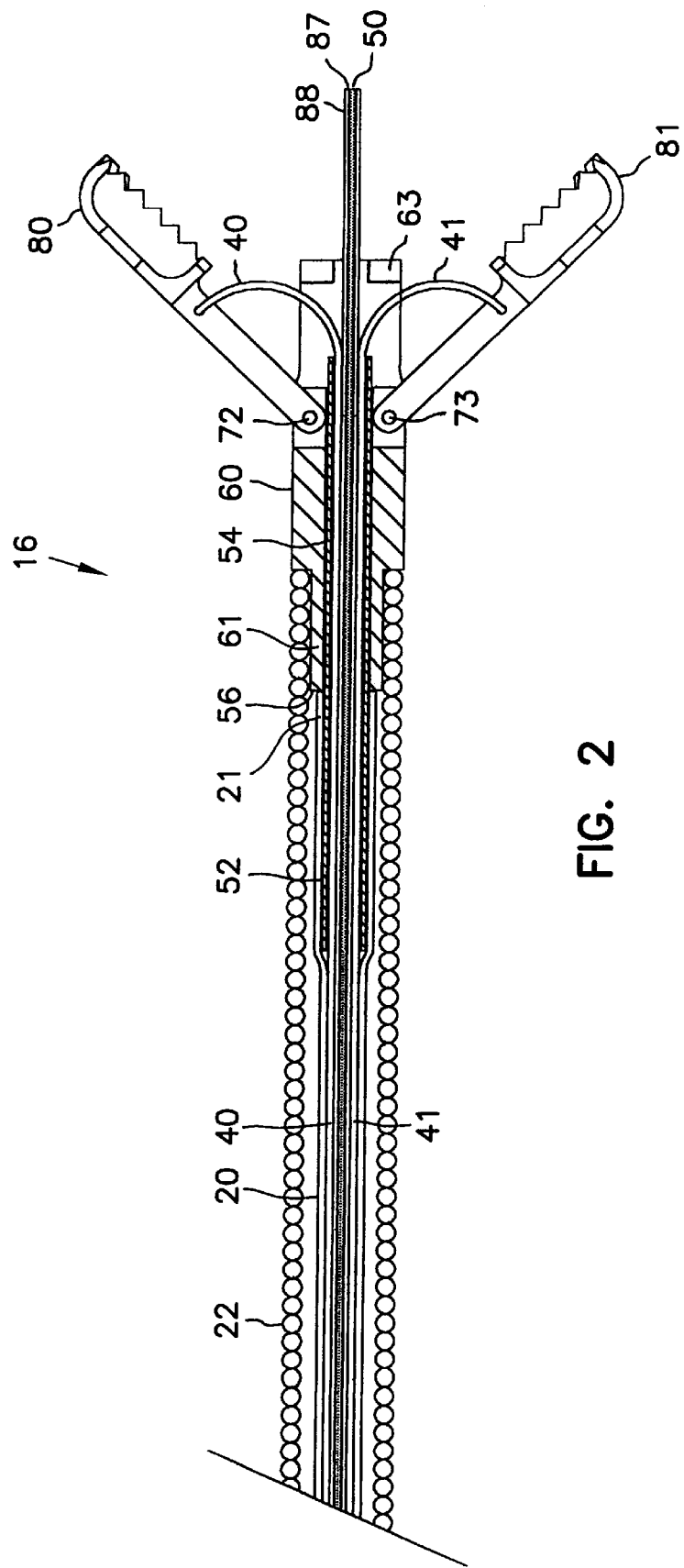
FIG. 2 is a cross-sectional view at an enlarged scale of the distal end of the forceps of FIG. 1, with the forceps jaws open.

As seen in the left portion of FIG. 2, the main body or length of the forceps 10 consists of coaxial inner and an outer tubular members. In one preferred embodiment, the inner tubular member is a hollow plastic tube 20, and the outer tubular member or catheter body is coil 22. The coil 22 is a finely wound spiral coil of stainless steel as is generally known and used in catheters and guidewires. Alternatively, the outer tubular member could be made using another plastic tube, or a plastic/metal composite structure, in place of coil 22. The plastic tube 20 is positioned within coil 22 and these components are dimensioned with respect to each other so that tube 20 may be free to move axially within coil 22 during actuation of the jaws, as is explained below.

Positioned within inner tube 20 are a pair of control wires 40, 41, and the optical fiber 50. These components, together with outer coil 22 and inner plastic tube 20 extend over the main length of the device, from the distal end 16 to the handle portion 12. At the handle, coil 22 and tube 20 pass through a plastic sleeve 24, which serves as a reinforcement and strain relief, into a bore 25 in the tip 13 of the handle 12. The plastic sleeve 24 and the proximal end of the coil 22 are received and secured, as by bonding, in the tip 13 of the handle 12.

The inner plastic tube 20, control wires 40, 41 and fiber 50 are not secured at tip 13, but pass through bore 25, through a stainless steel reinforcing tube 29 to slider 30, which is movably received in a slot 28 in handle 12. Reinforcing tube 29, tube 20 and control wires 40, 41 are secured to slider 30 which together form an actuator mechanism for the forceps 10. Movement of slider 30 causes axial movement of reinforcing tube 29, tube 20 and control wires 40, 41 relative to coil 22, which is used to actuate the cutting jaws. Loops 26 and 27 are provided in handle 12 and slider 30, to form finger holes useful in grasping and manipulating the forceps.

Optical fiber 50 extends through slider 30, and out of handle 12, in a protective cable or sheath 32, for connection to electro-optical units (not shown) which provide the illumination light to the fiber, and which receive and analyze the returned right from the target at distal the end of the forceps. The optical biopsy forceps of the present invention may be used with any type of electro-optical technique for guiding the forceps. This may include systems which use viewing or imaging, systems which use illumination with white light to excite dyes in the area of interest, and spectroscopic techniques to identify tissue types by spectral analysis of light returned from tissue illuminated with light of certain wavelengths. Such spectroscopic techniques utilize the property of certain tissue types to reflect or fluoresce light having characteristic wavelengths.

As seen in FIGS. 2, 5A, 5B and 5C, the distal end 16 of the optical forceps includes a yoke 60, which serves as a mounting member for the cutting jaws. Yoke 60 may be machined from stainless steel or formed of other suitable material. It generally has a proximal portion or section indicated by reference number 61, a center section 62, and a distal section 63 having inwardly curved opposing distal end portions 63a and 63b. Yoke 60 has a bore 64 running therethrough. Each of the opposing distal end portions 63a and 63b has an arc shaped groove 65 (FIGS. 5B and 5C) formed therein which defines a guide slot for the distal end of the fiber 50. The diameter of the bore defined by the arcuate grooves 65 can be stepped to a smaller size at distal end portions 63a and 63b. Sections 61 and 62 are generally circular in section. Section 61 has a diameter corresponding to the inside dimension of coil 22, while section 62 has a diameter corresponding to the outside dimension of coil 22, so that the end of coil 22 may be received and bonded to section 61. The proximal end surface 56 of the yoke 60 cooperates with the distal end 21 of the inner tube 20 to provide a limit stop for the fiber tube assembly 52 when it is being advanced within the outer tube 22 to open the jaws. Center section 62 has a pair of holes 68, 69 which receive pins 72, 73 to hold the jaws in place.

Figure 3:
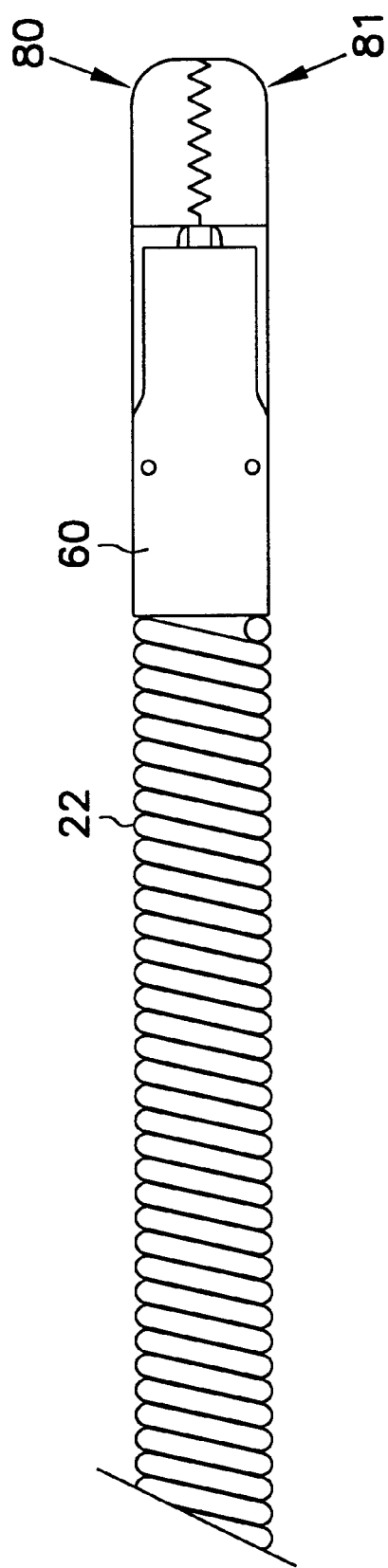
FIG. 3 is a view of the distal end of the forceps of FIG. 1, with the forceps jaws closed.
Figure 4:
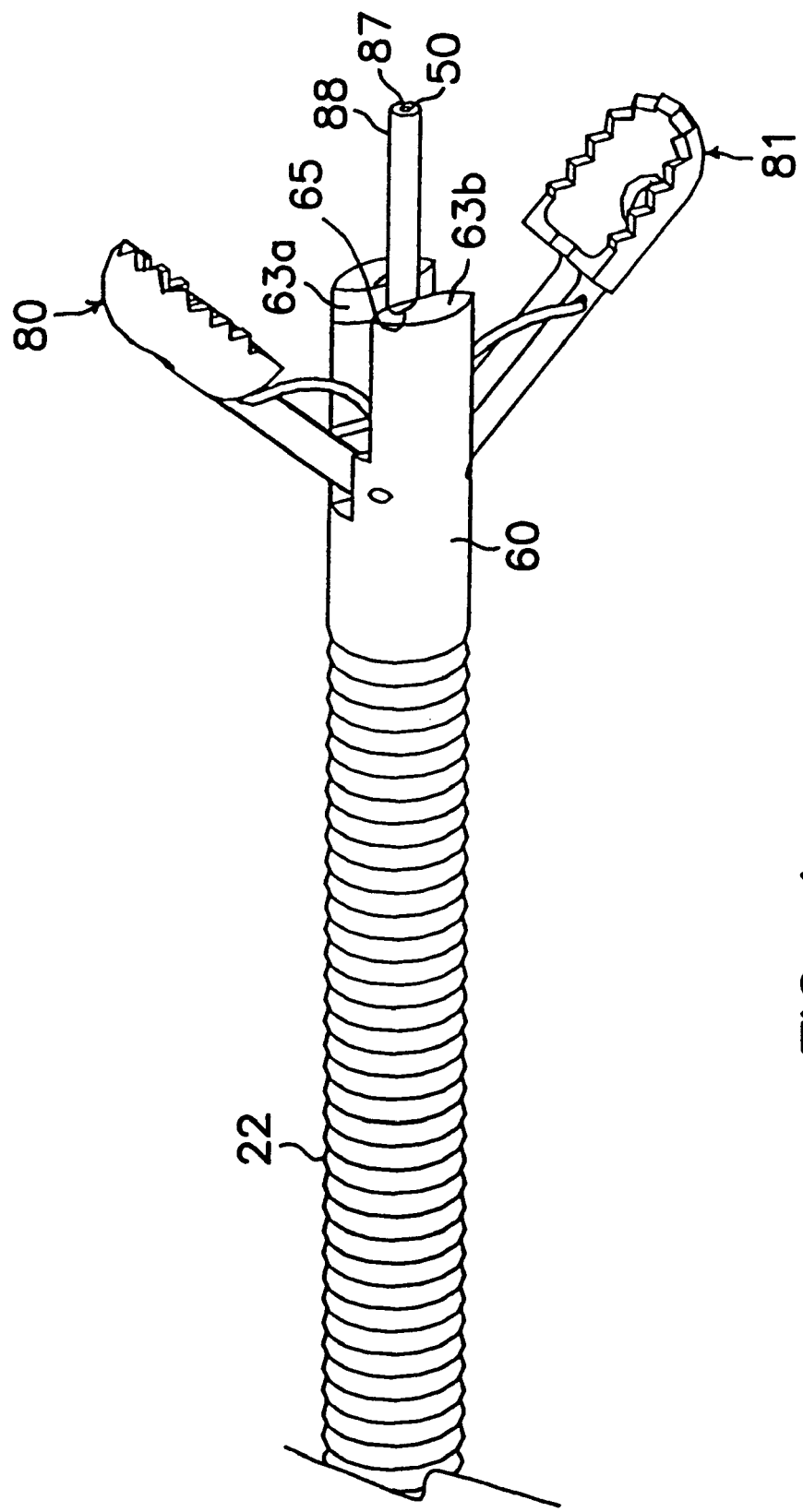
FIG. 4 is a perspective view of the fiber tube assembly and related components, for the distal end of the device of FIG. 2.
Figure 5C:
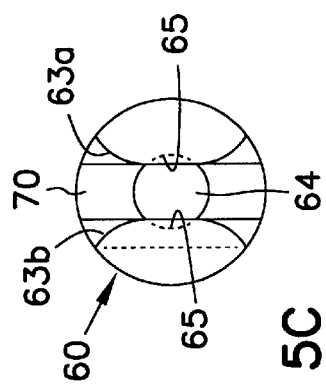
FIG. 5C is an end view of the component of the distal end of the device of FIG. 2.
Figure 5A:
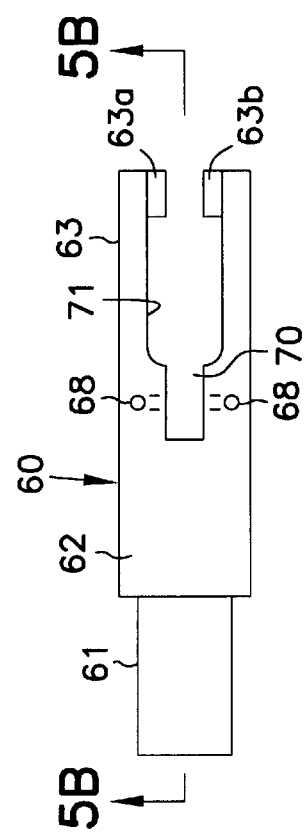
FIG. 5A is a top view, at an enlarged scale, of a component of the distal end of the device of FIG. 2.
Figure 5B:
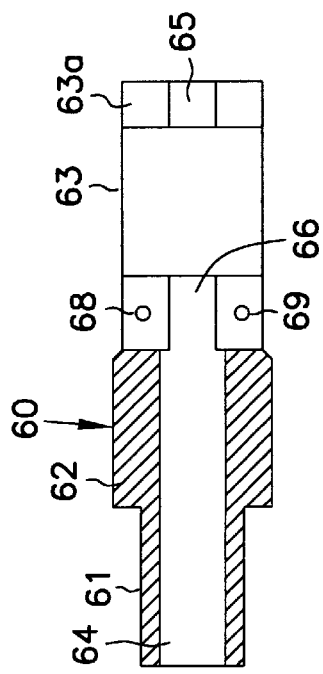
FIG. 5B is a side sectional view taken along the line 5B—5B of FIG. 5A.

Distal section 63 is stepped down relative to section 62, as seen in side view in FIGS. 2 and 5B, to allow the jaws 80 and 81 to fold against it when the jaws are closed (FIG. 3) so as to have a thin profile for ease of introduction and navigation. Distal section 63 also has a vertical slot 70 provided therein which is dimensioned to the size of the mounting ends of the lever arms 85 of the jaws. The inner wall 71 of distal section 63 is stepped outwardly relative to the slot 70 to provide clearance for the ends of control wires 40 and 41.

Figure 6A:
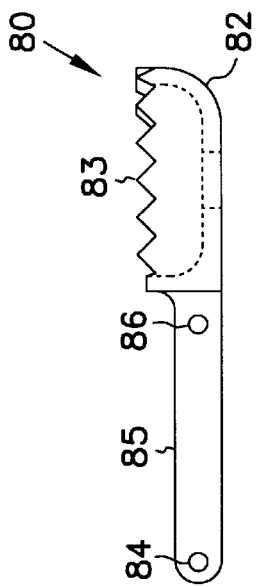
FIGS. 6A and 6B are top and side views, respectively, of a cutting jaw component of the distal end of the device of FIG. 2.
Figure 6B:
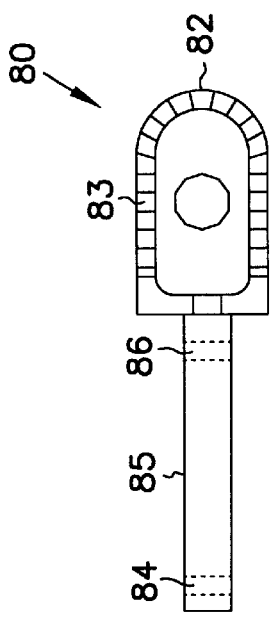

Because jaws 80 and 81 are similar only one is described in detail here. The two jaws are mirror-image identical, but with their serrations staggered so that they will mesh. As seen in FIGS. 6A and 6B, jaw 80 has a rearward lever or mounting portion 85, and a distal cup or sample receiving portion 82, which has sharp serrations 83 used to cut the tissue sample. The lever portion 85 has a hole 84 formed to receive the pin 72 which thus serves to retain the jaws, and also to acts as the pivot point. A hole 86 is provided at the forward apex of the relieved section, to receive the end of control wire 40 (or 41) which is crimped or bent at a right angle at its tip to be effectively captured. The control wires are formed of wire which is stiff enough to push against the jaws to open them, but flexible enough to flex as the wires are retracted to pull the jaws together.

As seen in FIG. 2, the distal end 16 of the optical forceps also includes a fiber tube assembly 52. It includes a tube 54 which may be machined from stainless steel, or formed of other suitable material. The end of plastic tube 20 overlaps end 55 of the tube 54 and is bonded to tube 54. The control wires 40, 41 and the optical fiber 50 pass into it from the plastic tube 20. The optical fiber and the control wires pass axially through the tube 54 and are bonded to the tube 54 by epoxy or other suitable adhesive. The optical fiber 50 includes a jacket 87 of polyamide or similar material and an outer protective tube 88 made of stainless steel, for example. The jacket 87 extends the length of the optical fiber from its proximal end to its proximal end. The protective tube 88 extends from the distal end of the optical fiber to at least a point located within the distal end of tube 54. The distal end of the optical fiber 50 is flush with the end of the protective tube 88, and may have a lens or clear epoxy coating, depending on the optical properties desired. The protective tube 88 at the distal end of the optical fiber is designed to give strength to prevent damage to the fiber by tweezers and the like when tissue is removed from the biopsy jaws.

Referring to FIGS. 1 and 2, in operation, the slider 30 is retracted toward the back of handle 12 to close the jaws. This causes movement (to the left in FIG. 2) of plastic tube 20, the fiber tube assembly 52, the control wires 40, 41, and the optical fiber 50. This retracts the optical fiber into the yoke 60 and the pulling of the control wires closes the jaws. In this configuration, the distal end is of the same narrow diameter as the main body of the forceps catheter, and the closed jaws have a smooth, rounded shape to facilitate introduction and navigation in the vascular, endoscopic or laproscopic systems. Also, the cutting jaws are coaxially positioned with respect to the distal end of the optical fiber.

Once in place in the general area of interest, the forceps jaws can be opened by pushing slider 30 of the control handle forward. This causes movement (to the right in FIG. 2) of plastic tube 20, the fiber tube assembly 52, the control wires 40, 41, and the optical fiber 50. The control wires push against the jaws, causing them to open. Simultaneously, the tip of the optical fiber is axially extended. The distal end or tip of the optical fiber is positioned at the distal end of the catheter body with its optical view axis or view axis aligned for a tissue analysis zone adjacent the distal tip of the catheter body and positioned at the area of contact of the cutting jaws when the cutting jaws are operated to their closed cutting position. The device may then be used for optical tissue identification. When an area of disease is identified and a biopsy of it is needed, slider 30 is pulled, retracting the tip of the fiber and simultaneously causing the jaws to close and cut a biopsy sample at the exact place being viewed by the fiber. The biopsy sample is cut from the exact tissue site identified by the spectroscopic analysis step without requiring moving or repositioning of the catheter body. The forceps may then be withdrawn from the patient to recover the sample for analysis. The analysis of the withdrawn sample can be conducted using known laboratory techniques to confirm the identification of the tissue sample made by spectroscopic analysis.

The optical biopsy forceps of the invention is used for spectroscopically analyzing tissue in the tissue analysis zone adjacent the distal end of the forceps through the use of an electro-optic tissue analysis system connected to the proximal end of the optical fiber. The optical biopsy forceps are guided spectroscopically within the body to an area of interest as identified by the spectroscopic analysis of tissue type in the tissue analysis zone adjacent the distal tip of the catheter body.

Figure 7:
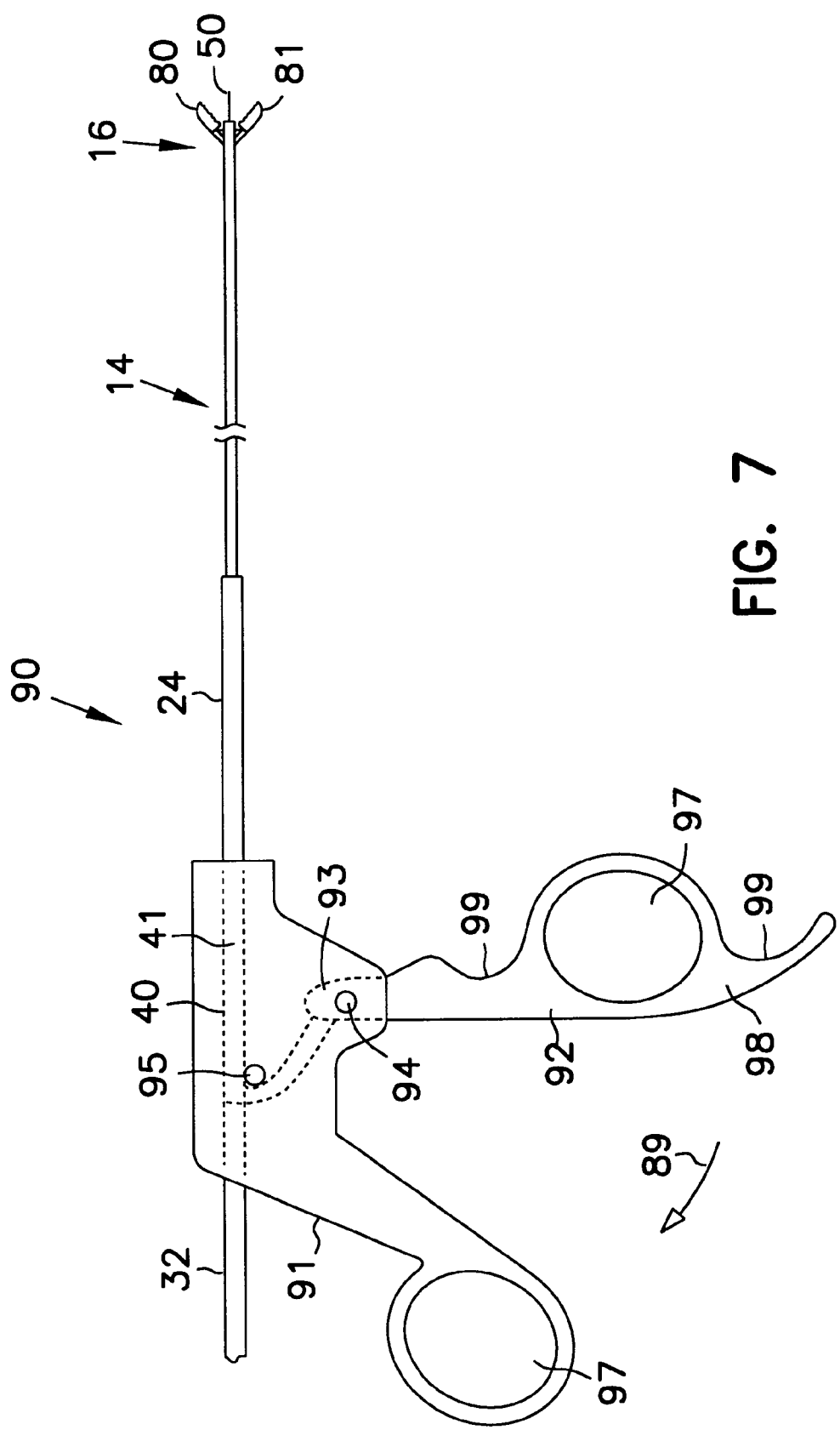
FIG. 7 is an overall view of another embodiment of the optical biopsy forceps according to the present invention.

Referring to FIG. 7, another embodiment of an integrated optical biopsy forceps of the present invention is generally indicated by reference number 90. The optical forceps 90 is generally similar to the optical forceps 10 shown in FIG. 1, and accordingly, corresponding elements have been given the same reference number. The optical biopsy forceps is adapted for use internally of the body, for example in connection with endoscopic, laparoscopic or vascular procedures. Forceps 90 includes a handle portion 91 and an operating lever 92 at the proximal end, a middle portion 14 which extends over the main length of the device, and a distal end 16. The distal end 16 includes forceps cutting jaws 80 and 81 and the distal end of the optical fiber 50 which is contained within a plastic tube, corresponding to plastic tube 20 of forceps 10, and pass through a sleeve 24 in the manner illustrated in FIGS. 1–6 for the forceps 10.

The operating lever 92 has its upper end 93 pivoted to the handle 91 by a pivot pin 94. The forceps 90 includes a reinforcing tube, corresponding to reinforcing tube 29 of forceps 10, which encloses the fiber optical tube, and control wires 40 and 41. The control wires pass around a post 95 and are secured to the operating lever 92 near its upper end 93 located within the handle. The optical fiber tube extends out of the handle in a protective sheath 32 as described above with reference to optical biopsy forceps 10. Loops 97 are provided in the handle 91 and the operating lever 92, forming finger holes useful in grasping and manipulating the forceps. The operating lever also has curved regions 99 forming finger rests, which together with the depending operating lever arrangement of the forceps 90, enhance the ergonomics of the instrument.

The jaws 80 and 81 are open when the relative position between the handle 91 and the operating lever 92 is as illustrated in FIG. 6. When the operating lever 92 is moved rearwardly toward the handle, in the direction of the arrow 89, the control wires 40 and 41 are drawn around the post 95, retracting the optical fiber and operating the jaws 80 and 81 closed in a manner similar to that described for the operation of forceps 10. When the operating lever is moved in the opposite direction, the control wires are advanced within tube 20, causing the jaws to open.

Figure 8:
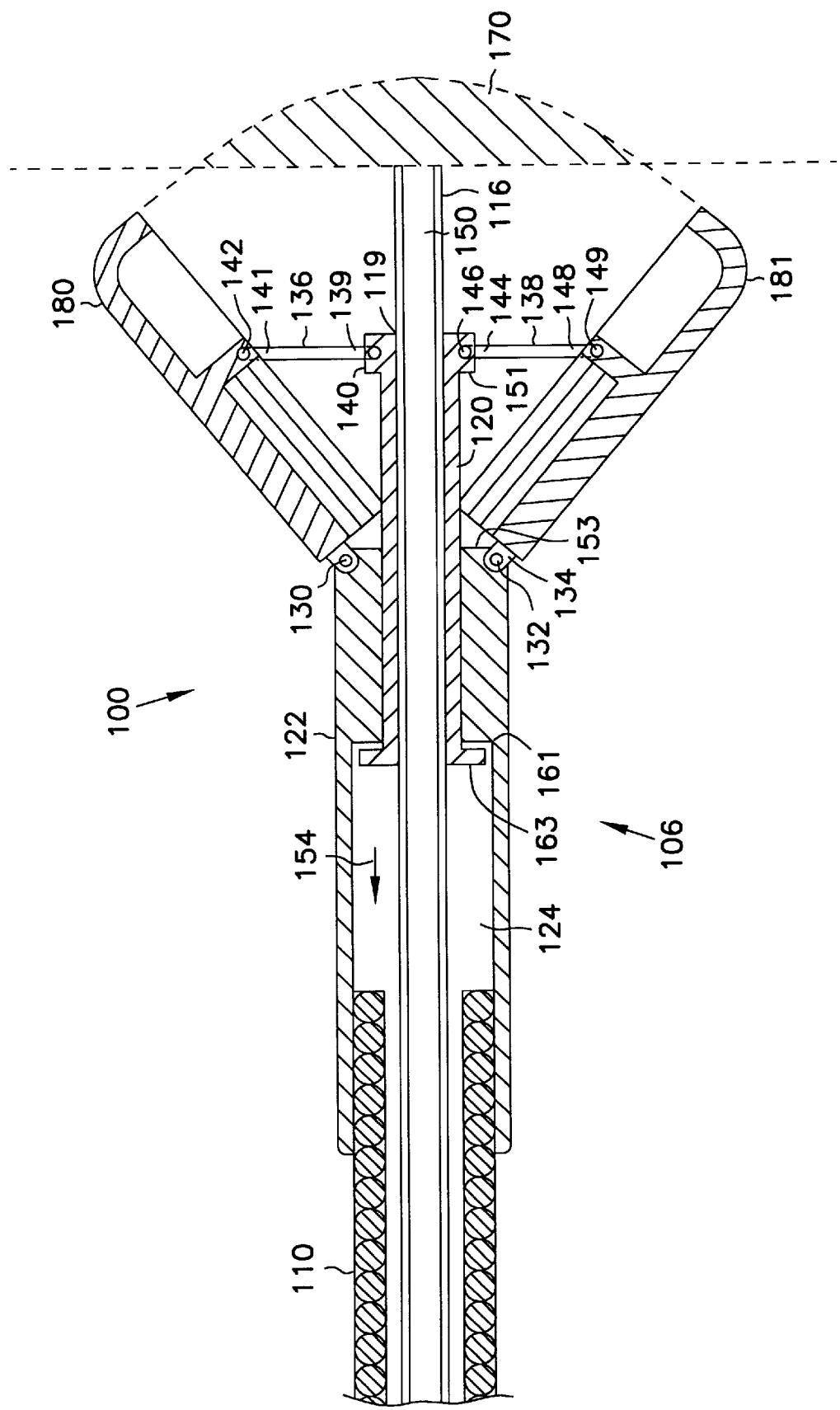
FIG. 8 is a cross-sectional view of the distal end of an optical biopsy forceps provided in accordance with a further embodiment of the invention.

Referring to FIG. 8, there is illustrated the distal end 106 of an integrated optical biopsy forceps provided in accordance with a further embodiment of the invention. The optical biopsy forceps includes an optical fiber 150 and opposed forceps cutting jaws 180 and 181, which can be similar to the optical fiber and the jaws of forceps 10 shown in FIGS. 1–6. The optical fiber 150 of the optical biopsy forceps includes an outer tubular, sheath-like member or catheter body 110, which corresponds to the outer sheath or coil 22 (FIG. 2), and a reinforcement cover 116, which, for example, can be a metal coil or cable, a nylon sheath, or any other suitable cover. The reinforced optical fiber is movable axially within the sheath 110. The optical biopsy forceps further includes a tubular slide member connected to the optical fiber and movable therewith, and coupled to the jaws 180 and 181 for actuating the jaws 180 and 181 as the optical fiber is moved within the outer sheath 110.

The optical biopsy forceps includes a suitable handle (not shown) for facilitating actuation of the tubular slide member 120. Preferably, the handle is similar to the handle 12 (FIG. 1) of the optical biopsy forceps 10, but the handle can include any type of actuating mechanism capable of imparting bidirectional axial movement to the optical fiber 150 of the optical biopsy forceps. Referring additionally to FIG. 1, in such arrangement, the optical fiber 150 positioned within the outer sheath, extends over the main length of the device, from the distal end 106 to the handle. The proximal end of the sheath 110 passes through a sleeve, such as sleeve 24, and is secured to the tip of the handle. The sleeve provides reinforcement and strain relief where the sheath 110 is attached to the handle. The proximal end of the optical fiber 150 also passes through sleeve 24 and is secured to the slider 30 of the handle 12 distally of the proximal end of the optical fiber 150, the end portion of which passes through the slider and out of the handle for connection to suitable electro-optical units in the manner that has been described for the optical fiber 50 of optical biopsy forceps 10. The slider 30 of the handle is adapted to push the reinforced optical fiber 150, which in turn pushes the tubular slide member 120, to open the jaws of the optical biopsy forceps and to pull the reinforced optical fiber, pulling the tubular slide member 120, to close the jaws.

The optical biopsy forceps of the present invention can be used with any type of electro-optical technique for guiding the forceps. This may include systems which use viewing or imaging, systems which use illumination with white light to excite dyes in the area of interest, and spectroscopic techniques to identify tissue types by spectral analysis of light returned from tissue illuminated with light of certain wavelengths. Such spectroscopic techniques utilize the property of certain tissue types to reflect or fluoresce light having characteristic wavelengths.

Considering the optical biopsy forceps in more detail, with reference to FIG. 8, the sheath 110 is a flexible hollow catheter which can be made a plastic tube, or a plastic/metal composite structure that defines an opening or bore therethrough. By way of example, the outer sheath 110 can be similar to those of disposable biopsy forceps commonly used with colonoscopes used in the upper and lower gastrointestinal tracts, and broncoscopes used in the trachea and bronchus. Alternatively, the outer sheath 110 can be a rigid tube, such as those of biopsy forceps commonly used with cystoscopes, colposcopes and laproscopes.

At its distal end, the optical fiber 150 extends through a central bore 119 formed through a tubular slide member 120 which, in turn, is mounted in a mounting member or jaw support block 122 which serves as a mounting member for the cutting jaws 180, 181. The jaw support block 122 can be machined from stainless steel or formed of other suitable material. The jaw support block 122 has a bore 124 running therethrough which is generally circular in section. The inner dimension of the jaw support block 122 corresponds to the outer dimension of the outer sheath 110 which is secured to the support block in a suitable manner, such as with cement or by crimping. The jaws 180, 181 are hinged to the support block 122 which has a pair of holes which receive pins 130, 132 which pass through ears 134 of the jaws to hold the jaws 180, 181 in place. The attachment of the jaws to the support block by ears 134, as seen in side view in FIG. 8, allows the jaws 180, 181 to fold against the front end of the support block when closed so as to have a thin profile for the distal end of the forceps for ease of introduction and navigation. The jaw support block 122 has a slot to control travel of the jaws 180 and 181.

The tubular slide member 120 is mounted in the bore 124 in the jaw support block 122 and is free to move axially within support block 122 during actuation of the jaws. The fiber 150 is secured to the tubular slide member 120 in a suitable manner such as with cement. The jaws 180, 181 are connected to the tubular slide member 120 by a pair of control links 136, 138, which are rigid members that function as a linkage mechanism connecting the cutting jaws to the tubular slide member. Control link 136 has one end 139 connected to tubular slide member 120 by a pin 140. The other end 141 of the control link 136 is connected to jaw 180 by a pin 142. Similarly, control link 138 has one end 144 connected to tubular slide member 120 by a pin 146 and its other end 148 connected to jaw 181 by a pin 149. Thus, axial movement of the optical fiber in the direction of arrow 154, as the optical fiber is retracted, causes axial movement of tubular slide member 120, pivoting the control links 136, 138, about their ends 139 and 144, respectively, drawing the jaws together to actuate the cutting jaws 180, 181. The rearward surface 151 at the distal end 152 of the tubular slide member 120 is adapted to engage the forward surface 153 of the jaw support block 122, functioning as a travel limit stop surface to limit the axial movement of the tubular slide member 120 during retraction of the optical fiber 150. Similarly, when the optical fiber 150 is advanced into the sheath 112, the tubular slide member 120 is moved axially in the opposite direction, causing the control links 136, 138 to move the jaws apart. The forward surface 161 at the proximal end 162 of the tubular slide member 120 is adapted to engage the rearward surface 163 of the jaw support block 122, functioning as a travel limit stop surface to limit the axial movement of the tubular slide member 120 during retraction of the optical fiber 150. Thus, both the proximal and distal ends of the tubular slide member 120 include limit stops which prevent both over distention and over retraction of the optical fiber 150.

Referring additionally to FIG. 1, in operation of the optical biopsy forceps, initially, the optical fiber 150 is fully retracted (by retracting the slider 30 toward the back of the handle) to move the tubular slide member 120 in the direction of the arrow 154 until its rearward surface 151 engages forward surface 152 of the jaw support block 122. In this position, the control links 136 and 138 have been drawn rearwardly, drawing the jaws 180, 181 together so that the jaws are closed. In this configuration, the distal end 106 of the forceps is substantially of the same narrow diameter as the outer sheath 116 which defines the main body portion of the optical biopsy forceps, and the closed jaws have a smooth, rounded shape to facilitate introduction and navigation through the biopsy channel of an endoscope, for example.

The endoscopist advances the optical biopsy forceps through the biopsy channel of the endoscope to the general area of interest, i.e., such as a tissue site or tissue analysis zone with a body, represented by the reference numeral 170. Once in place in the general area of interest, the forceps jaws can be opened by advancing the slider 30, thereby advancing the optical fiber 150 forwardly through the handle. This causes the tubular slide member 120 to move forwardly (to the right in FIG. 8), which in turn causes pivoting of the control links 136 and 138. As the control links pivot, the control links push against the jaws, causing the jaws to open. Simultaneously, the distal tip of the optical fiber 150 is axially extended forwardly beyond the jaws. The forceps may then be used for optical tissue identification.

When an area of disease is identified and if a biopsy of it is needed, the slider 30 is retracted, retracting the optical fiber 150 and thus the tubular slide member 120, retracting the tip of the optical fiber and simultaneously causing the jaws to close and cut a biopsy sample at the exact place that has been located by viewing through the optical fiber. To take the tissue sample, the endoscopist holding the instrument by the handle, gently pulls back on the slider of the handle, retracting the optical fiber and tubular slide member 120, moving the optical fiber away from the tissue surface. As the optical fiber is being retracted, the jaws begin to close as the tubular slide member is moved in the direction of the arrow 154. While the jaws are being closed, the endoscopist gently pushes on the instrument to urge the jaws towards the tissue surface so that a tissue sample will be captured by the jaws as they close. When the jaws are closed, the endoscopist pulls the entire assembly away from the tissue surface and then withdraws the optical biopsy forceps from the endoscope so that the specimen tissue can be retrieved.

Thus, the present invention has provided an optical biopsy forceps. An important feature of the invention is that the tip of the optical fiber 50 (and optical fiber 150) is coaxial with, and perfectly aligned with, the zone where the two jaws 80, 81 (and jaws 180, 181) intersect and the sample is taken. Thus, there is no offset or 'parallax' error between the spot where the optical measurements were taken and the spot from which the biopsy sample will be taken. This, together with the slim and compact profile of the device when the jaws are retracted, is a great improvement over prior art devices. In accordance with another feature, the fiber optic assembly, including the optical fiber and the tubular slide member of the biopsy forceps, can be produced as a disposable assembly, with the rest of the biopsy forceps being produced as a non-disposable unit. The major advantage of forceps 100 as compared to forceps 10 is, because the biopsy jaw control wires 40, 41 are not required, larger diameter optical fibers can be used to increase the detected signal relative to noise.

It will be appreciated from the foregoing that we have provided an improved optical biopsy forceps which provides the physician a greater degree of accuracy and control over the diagnosis process than was previously possible. While we have illustrated the invention with two illustrative embodiments of the invention, it will be appreciated that variations of shapes, materials and assembly are possible, within the scope of the invention.

What is claimed:

1. An integrated optical biopsy forceps, comprising:
    a flexible catheter body having a bore therethrough, and having proximal and distal ends;
    an optical fiber extending through the catheter body and adapted at its proximal end for connection to a electro-optic tissue analysis system, the distal end of the optical fiber positioned at the distal end of the catheter body with its optical view axis aligned for a tissue analysis zone adjacent the distal tip of the catheter body;
    cutting jaws mounted at the distal end of the catheter body for selective opening and closing in a biopsy cutting movement, ssaid cutting jaws coaxially positioned with the optical view axis, said cutting jaws having a closed cutting position on the optical view axis in the tissue analysis zone; and
    an actuator mechanism operatively connected to the jaws and extending to the proximal end of the catheter body for selectively controlling from the proximal end the opening and closing of the cutting jaws to cut a biopsy sample from the exact location of the optical tissue analysis zone, the actuator mechanism including control wires connected to the cutting jaws for causing opening and closing of the cutting jaws by axial movement of the control wires.

2. A forceps according to claim 1, wherein the actuator mechanism is operative to extend and retract the distal tip of the optical fiber as the cutting jaws open and close together.

3. The forceps according to claim 2, wherein the catheter body includes a tubular member coupled to the optical fiber, and wherein the actuator mechanism includes a slider mounted to the handle for movement relative thereto, the control wires being connected to the slider, the slider being operative to differentially push the tubular member to open the cutting jaws and extend the tip of the optical fiber and to pull the control wires and the tubular member to retract the tip of the optical fiber and close the cutting jaws in taking a biopsy sample.

4. The biopsy forceps as recited in claim 1, wherein the actuator mechanism includes a slider mounted to the handle for movement relative thereto, and the control wires are connected to the slider.

5. The biopsy forceps as recited in claim 4, wherein the slider is operative to differentially push the tubular member to open the cutting jaws and to pull the control wires and the tubular member to close the cutting jaws in taking a biopsy sample.

6. The biopsy forceps as recited in claim 1, further comprising a yoke at the distal end of the catheter body, where the cutting jaws are mounted on the yoke.

\* \* \* \* \*